United States Patent
Strong

[19]

[11] Patent Number: 6,048,308
[45] Date of Patent: Apr. 11, 2000

[54] VAGINAL SPECULUM

[76] Inventor: John E. Strong, 732 Reber Ave., Waterloo, Iowa 50701

[21] Appl. No.: 09/281,380

[22] Filed: Mar. 30, 1999

Related U.S. Application Data

[60] Provisional application No. 60/103,076, Oct. 5, 1998.

[51] Int. Cl.[7] .................................................. A61B 17/00
[52] U.S. Cl. ........................... 600/205; 600/220; 600/222; 600/223; 600/224
[58] Field of Search ...................................... 600/214, 219, 600/220, 221, 223, 224, 205, 235, 245, 226, 222

[56] References Cited

U.S. PATENT DOCUMENTS

| | | | |
|---|---|---|---|
| 1,614,065 | 1/1927 | Guttmann | 600/235 |
| 3,716,047 | 2/1973 | Moore et al. | 600/223 X |
| 4,052,980 | 10/1977 | Grams et al. | 600/224 |
| 5,499,964 | 3/1996 | Beck et al. | 600/220 |
| 5,868,668 | 2/1999 | Weiss | 600/221 X |
| 5,873,820 | 2/1999 | Norell | 600/220 |

FOREIGN PATENT DOCUMENTS 549791  12/1942  United Kingdom ................... 600/224

OTHER PUBLICATIONS

Welch Allyn Kleenspec Disposable Vaginal Specula brochure (undated).

*Primary Examiner*—Jeffrey A. Smith
*Attorney, Agent, or Firm*—Allan L. Harms

[57] ABSTRACT

An improved single use vaginal speculum with lateral retracting bills is disclosed. Each of the lateral retracting bills is supported on an axially rotatable shaft mounted to a side of the yoke of the lift mechanism which raises the lower bill assembly away from the lower bill and handle member. The lateral bills separate by action of levers which are moved when the upper bill is rotated about its pivot on the yoke. The lift mechanism may be slid along a channel in the handle when a push button is depressed and latched when the push button is released. The observation opening of the vaginal speculum is enlarged and the lateral bills are supported to prevent their obstructing the observation of the user in examining the cervix and vaginal walls. The handle mounted to the lower bill is rotated rearward from a perpendicular and finger indentations are formed around the handle. A reservoir is formed in the lower bill and an evacuation duct extends from the reservoir to the exterior of the handle to allow suction of liquids from the reservations. A fiber optic cable is passed through the handle and is fixed to the upper concave surface of the lower bill and is terminated away from the distal end of the lower bill to direct light from the fiber cable toward the interior of the vagina.

23 Claims, 6 Drawing Sheets

VAGINAL SPECULUM

CROSS REFERENCE TO CO-PENDING PROVISIONAL APPLICATION

This application is converted from copending provisional patent application entitled "Vaginal Speculum", Ser. No. 60/103,076 filed Oct. 5, 1998. The disclosure of provisional patent application Ser. No. 60/103,076 is hereby incorporated in its entirety.

BACKGROUND OF THE INVENTION

In the physiological examination of the female reproductive organs, it is useful to visualize the inside of the vaginal space and the cervix. In such a physical examination, it is imperative that the view be as unobstructed and well illuminated as possible. Well illuminated visualization is also desired when procedures such as colposcopy, cervicoscopy, endometrial ablation are performed. Current appliances for accomplishing vaginal visualization include retractors which have a pair of vertically opposing blades which may be inserted into the vaginal opening and then separated. The lower blade is fixed perpendicularly to a handle and the upper blade is pivotable about the proximal end of the upper blade and may thereby be rotated away from the lower blade. Such vaginal specula also may be provided with an adjustment mechanism which allows the pivot point of the upper blade to be moved upward and away from the lower blade such that the opening between the proximal ends of the blades may be increased. An example of such a device is shown in U.S. Pat. No. 3,985,125.

Other devices include attachments for heating the blades, or for testing vaginal fluids, or for illuminating the vaginal vault, as shown in U.S. Pat. Nos. 5,231,973 and 5,465,709. None of these devices provide means to further open the vaginal opening and to separate the tissues of the vaginal opening in a transverse fashion.

Current practice utilizes a separate curved retractor instrument having blades that are inserted in the opened speculum and then locked in a spread position to displace the lateral tissues of the vulvular opening.

SUMMARY OF THE INVENTION

The present invention provides an improved disposable vaginal speculum which displaces the tissues of the vaginal opening in both a vertical and transverse manner. The invention also provides improved illumination of the vaginal space and for evacuation of liquids which may be collected in the fixed lower bill of the vaginal speculum. The invention also provides an improved lift control mechanism which can be manipulated without annoying clicks and can be operated with one hand.

The invention is provided with a handle having a lower bill fixed thereto at an angle somewhat greater than perpendicular. A top bill is pivotable relative to the proximal end of the lower bill such that the upper bill and lower bill may be spread to allow visualization of the vaginal cavity once the upper and lower bills have been inserted in the vaginal vestibule. A lift mechanism is slidable along the handle and may be locked in place at selective locations such that the proximal ends of the upper bill and the lower bill may be spaced apart after the bills have been placed in the vaginal opening. The lift mechanism includes a slider which is slidable in a longitudinal slot in the handle. The slider is provided with a "wishbone" yoke at its upper end, the yoke supporting the pivot of the upper bill relative to the handle.

The slider is provided with a thumb operated pad which may be displaced laterally to engage one of multiple posts formed on the interior of the handle in order to lock the slides at a selective place along the longitudinal slot in the handle.

The yoke of the lift mechanism also supports an axially rotatable, generally vertically oriented shaft on each of its sides. Each of the shafts is fixed to a generally horizontally extending lateral paddle which rests between the upper and lower bills. The lateral paddles are in opposition and are operable to spread the side tissues of the vaginal opening after the speculum has been inserted in the vaginal opening, and after the lift mechanism is raised to an operative position and the upper bills are spread apart.

The lateral paddles are operated by action of levers extending from the lower end of each of the rotatable shafts. The levers are shaped such that their displacement toward the handle causes rotation of each vertically oriented shaft and resulting separation of the lateral paddles. Because the lateral paddles are supported on the shafts which are rotatably supported on the outside of the legs of the yoke of the lift mechanism, the opening through the space between the bills is unobstructed.

Each lever attached to the end of one of the vertical shafts is moveable within a slot formed in a guide plate which is mounted to the lift mechanism slider. The guide plates are joined and positioned such that the levers will be displaced by movement of a lever which causes the upper bill to be displaced upwardly about its pivot mounting.

The invention speculum further includes a length of fiber optic cable fixed at one end to the lower bill and passing along the interior of the handle and terminating in a fiber optic cable coupler extending below the handle.

An evacuation duct is formed in the handle and opens into a funnel structure at the junction of the lower bill to the handle. The opposing end of the evacuation duct extends from the handle such that a suction tube may be coupled to it.

It is therefore an object of the present invention to provide an improved vaginal speculum which may be discarded after usage and which provides improved visualization of the cervix and the interior of the vaginal cavity.

It is also an objective of the invention to provide an improved vaginal speculum which allows the vertical and lateral dilation of the vaginal opening without the use of a separate retractor instrument.

It is further an object of the present invention to provide a vaginal speculum which permits lateral and vertical dilation of the vaginal opening by use of a single hand of the examiner.

It is further an object of the invention to provide a vaginal speculum with an improved lift mechanism which may be operated without removing the user's hand from the handle of the vaginal speculum and without creating annoying clicking sounds.

It is further an object of the invention to provide a vaginal speculum which is provided with a fiber optic light source for improved illumination of the uterine cavity into which the vaginal speculum is inserted.

It is further an object of the invention to provide a vaginal speculum which is equipped with a collector and evacuation tube within its handle to collect and evacuate liquids which are accumulated within the lower bill of the vaginal speculum.

It is yet another object of the invention to provide a vaginal speculum which is of reduced discomfort to the patient on which it is being used.

These and other objects will be best understood from examination of the detailed description which follows.

DETAILED DESCRIPTION OF THE INVENTION

Figure 1:
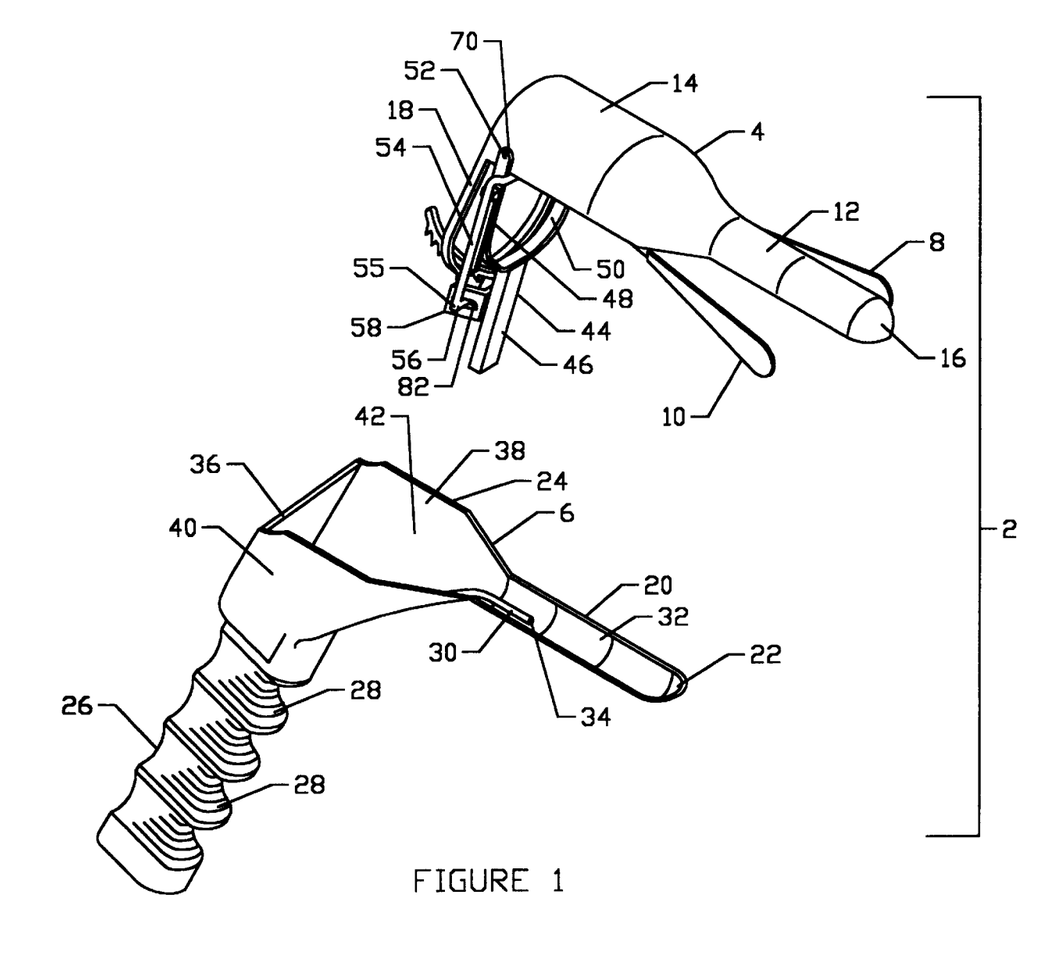
FIG. 1 is an exploded perspective view of the preferred embodiment vaginal speculum of the present invention.

In FIG. 1, the preferred embodiment of the single-use vaginal speculum 2 according to the invention is shown in exploded perspective with upper bill member 4 separated from lower bill member 6. Vaginal speculum 2 is preferably made of a suitable plastic. First and second lateral bill members 8, 10 of upper bill member 4 are shown in their fully retracting state. Upper bill member 4 comprises an upper bill 12 with a rounded distal end 16 designed to be inserted into the vaginal opening for examination purposes. Upper bill member 4 includes an enlarged proximal segment 14 having a downwardly depending frame 18 integrally formed therewith. Frame 18 is disposed angularly from the axis of upper bill 12 at an angle of approximately 130 degrees.

Pivotally connected to upper bill 12 is wishbone-shaped yoke 44 which includes slide bar 46 depending from spaced apart arms 48, 50 of yoke 44. Upper bill 12 is pivotable upon yoke 44 about pivot pin 52.

Second lateral bill 10 is fixed to a shaft 54 which is axially rotatable, shaft 54 being generally vertically disposed while axis of lateral bill 10 is generally horizontally disposed in use. A lever 56 extends generally perpendicularly from the lower end 55 of shaft 54. Lever 56 extends into slot 82 of guide frame 58. Shaft 54 is retained to leg 48 of yoke 44. First lateral bill 8 is similarly equipped.

Lower bill member 6 comprises a lower bill 20 having a curved distal end 22 which may be inserted into the vaginal opening. Lower bill 20 is joined to collector section 24 of lower bill member 6 which also comprises handle 26 which depends from collector section 24 at greater than 90 degrees, preferably approximately 130 degrees, from the axis of lower bill 20. Handle 26 is provided with finger indentations 28 to receive the fingers of the user when the handle 26 is held for insertion of upper bill 12 and lower bill 20 into the vaginal opening.

A fiber optic cable 30 is disposed within the upper concave surface 32 of lower bill 20 with light emitter end 34 spaced back from and directed toward curved end 22 of lower bill 20. Fiber optic cable 30 is preferably flexible and extends through collector section 24 of lower bill member 6 and passes through the interior of handle 26. A generally planar end wall 36 cooperates with sidewalls 38, 40 of funnel segment 24 to provide a reservoir 42 within funnel segment 24.

Figures 2, 3:
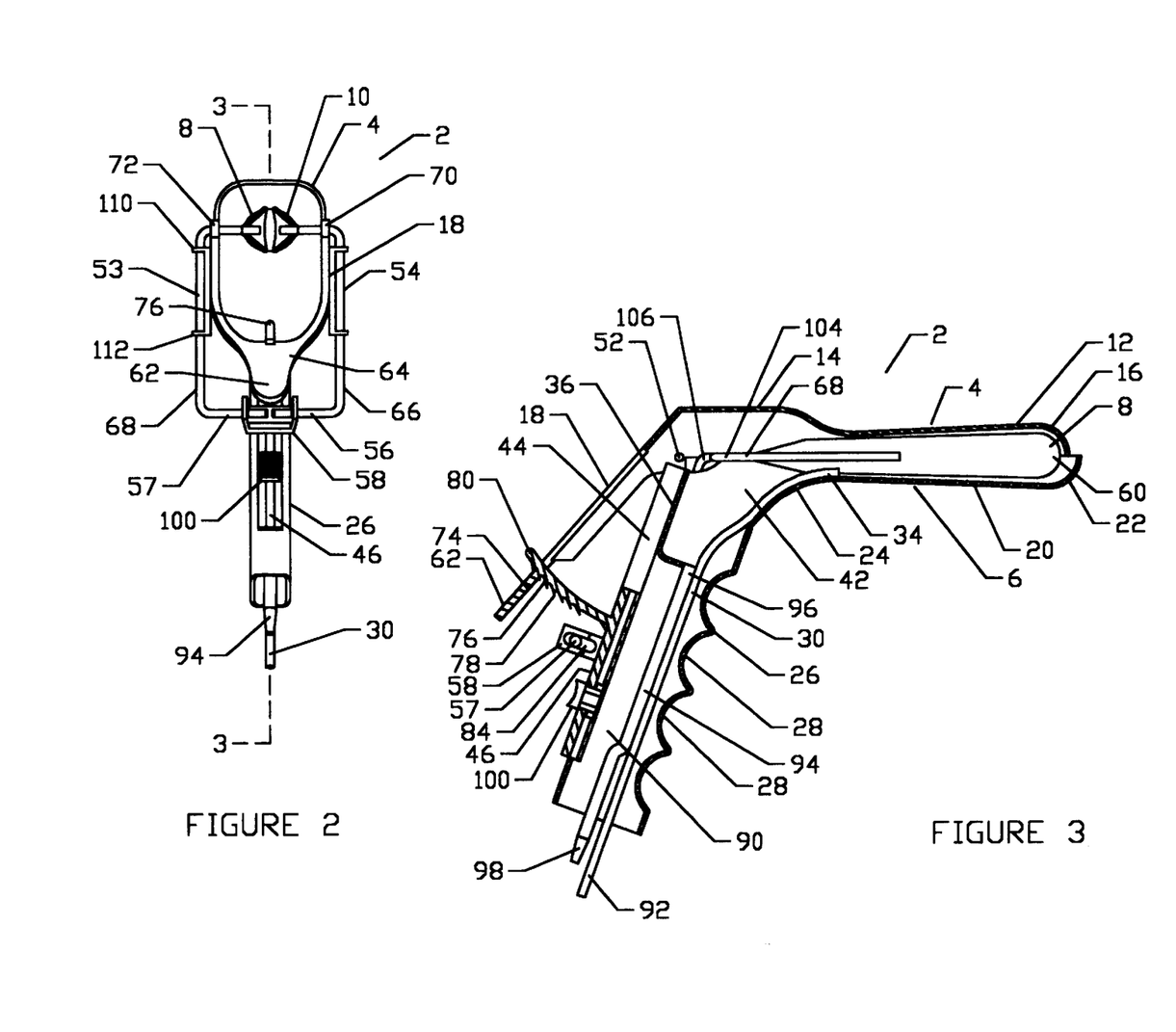
FIG. 2 is a front elevation of the preferred embodiment vaginal speculum shown in fully closed position.
FIG. 3 is a cross section taken along line 3—3 of the preferred embodiment vaginal speculum of FIG. 2.
Figure 4:
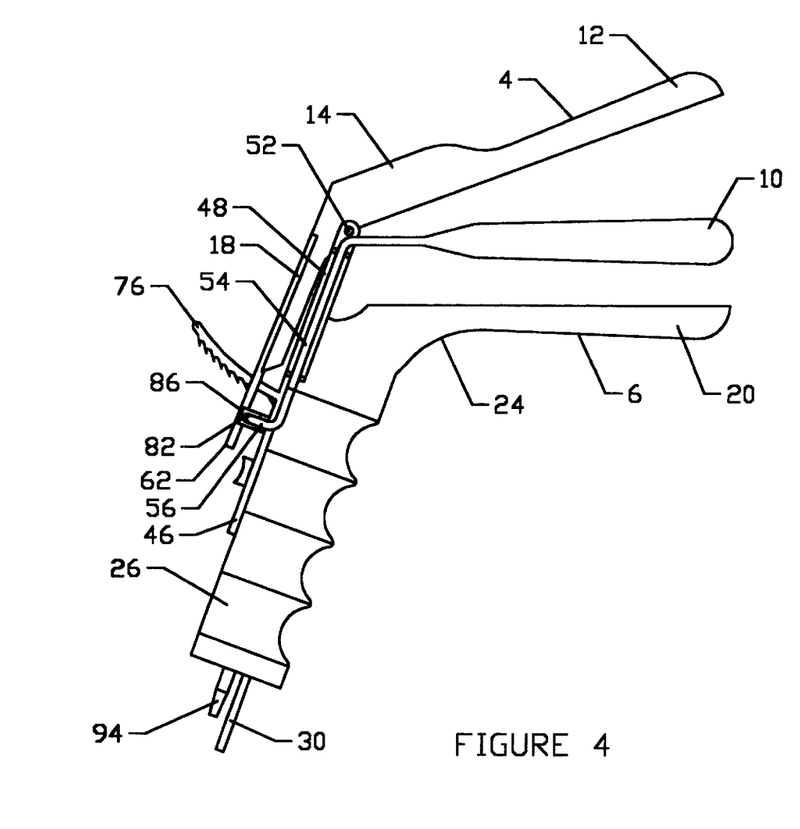
FIG. 4 is a side plan view of the preferred embodiment vaginal speculum shown with its lift mechanism raised and with upper bill rotated to its maximum opening and with the lateral blades fully separated.

Referring now to FIGS. 2–4, additional detail of the vaginal speculum 2 may be visualized. Upper bill member 4 is shown in its closed position in FIGS. 2 and 3 with upper bill 12 resting in abutment upon lower bill 20. With upper bill 12 in its closed position, lateral blades 8 and 10 are also in a closed position with their distal ends 60 in touching engagement. Frame 18 of upper bill member 4 is disposed in a spaced apart relationship to handle 26. Frame 18 is provided with tab lever 62 at the lower end 64 thereof which, when vaginal speculum 2 is in its fully closed position, is spaced from levers 56, 57 of lateral bill assemblies 66, 68. However, the user may depress tab lever 62 thereby causing upper bill 12 to pivot about pivot pin 52 on the upper ends 70, 72 of arms 48, 50 respectively of yoke 44. As frame 18 rotates toward handle 26 when tab lever 62 is urged toward handle 26, bottom bar 74 of frame 18 acts as a pawl against ratchet arm 76 which extends from slider bar 46 of yoke 44.

Bottom bar 74 may be selectively disposed against one of teeth 78 along underside of ratchet arm 76. Frame 18 is sized appropriately to cause bottom bar 74 to touchingly engage the underside of ratchet arm 76 at all times unless the user exerts upward pressure upon free end 80 of ratchet bar 76 thereby disengaging bottom bar 74 from teeth 78 and allowing upper bill 12 to return to its closed position with upper bill 12 resting on lower bill 20.

Lateral bill 8 is supported on a spine 104 which joins lateral bill 8 to shaft 53. An integral curved link 106 interconnects spine 104 to shaft 53 allowing shaft 53 to be mounted by brackets 110, 112 to arm 50 of yoke 44 while permitting lateral bill 8 to rest between upper bill 12 and lower bill 20 when tab lever 62 is not in touching engagement with lever 57. Shaft 53 is free to axially rotate within brackets 110, 112. Lateral bill 10 is similarly supported.

Figure 5:
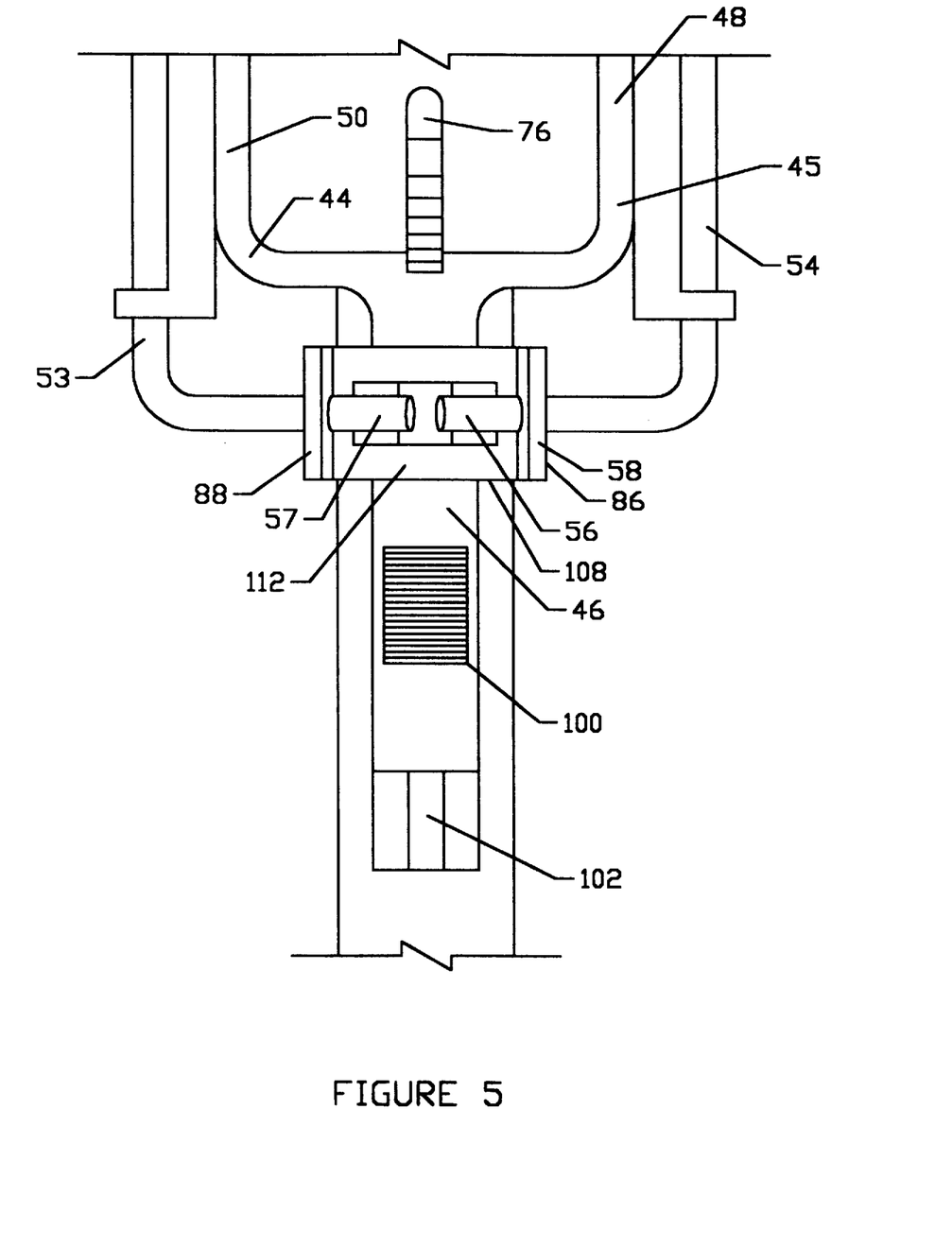
FIG. 5 is partly cut away enlarged view of the lift mechanism and lateral blade control levers of the preferred embodiment vaginal speculum.
Figure 6:
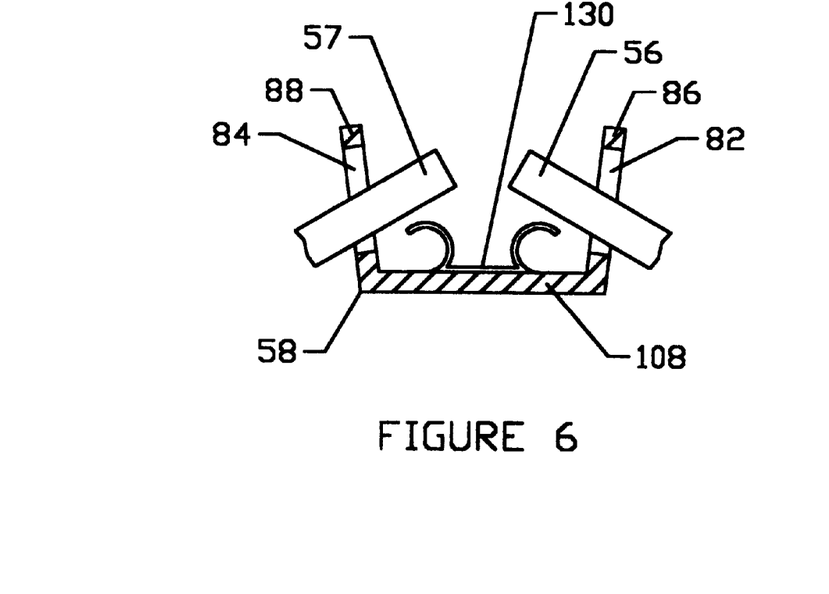
FIG. 6 is an enlarged section view of the guide frame of the lift mechanism of the invention.

Referring additionally to FIGS. 5 and 6, each sides 86, 88 of guide frame 58 is provided with a slot 82, 84 respectively into which one of levers 56, 57 are received. Slots 82, 84 are generally axially perpendicular to the longitudinal axis of handle 26 and serve to guide the movement of levers 56, 57. As levers 56 and 57 are displaced by tab lever 62 toward handle 26, shafts 53, 54 axially rotate in opposing directions of rotation, thereby causing lateral bills 8, 10 to separate spatially. Hence lateral bills 8, 10 may serve as transverse retractor blades against the sidewalls of a vaginal opening into which upper and lower bills 12,20 have been inserted.

The action of teeth 78 upon bottom bar 74 of frame 18 retains frame 18 at a selected position in its rotative range about pivot pin 52 and similarly depresses levers 56, 57 thereby rotating shafts 53, 54 and moving lateral bills 8, 10 apart.

The separation between arms 48 and 50 of yoke 44 is selected preferably in the range of 32 to 45 millimeters to permit facilitated visualization into the vaginal cavity when vaginal speculum 2 is inserted in the vaginal opening. Similarly the lateral spacing within frame 18 is preferably also in the range of 32 to 45 millimeters. Even though the widths of yoke 44 and frame 18 are enlarged, upper bill 12 and lower bill 20 are selected in size to comfortably be inserted in the vaginal opening. It should be understood that upper bill 12 and lower bill 20 may be selected in size depending the physiology of the patient to be examined.

The cross section view of FIG. 3 discloses that fiber optic cable 30 is disposed along the upper concave surface 32 of lower bill member 6 and passes through the hollow interior 90 of handle 26. Fiber optic cable 30 extends to a free end 92 exterior of handle 26 to which a light source may be attached. Light may then be transmitted along fiber optic cable 30 to emanate from light emitter end 34 of fiber optic cable 30 and thereby illuminate the vaginal cavity into which upper and lower bills 12, 20 have been inserted.

Collector section 24 of lower bill member 6 is provided with a planar end wall 36 such that fluids collected by lower bill 20 may drain into reservoir 42 of collector section 24 and be drained or suctioned via duct 94 which communicates at its first end 96 with reservoir 42 and has a coupling end 98 to which suction means may be coupled.

Handle 26 is provided with button 100 which is used to lock slider bar 46 at a selected location along longitudinal channel 102 of handle 26.

Referring to FIG. 4, a side plan view of the preferred embodiment is shown with slider bar 46 moved to its highest position along handle 26. Bottom bar 74 of frame 18 is retained by ratchet arm 76 such that frame 18 abuts handle 26 and upper bill 12 is at its maximum separation from lower bill 20, upper bill member 4 having been maximally rotated counterclockwise about pivot pin 52. Levers 56, 57 are displaced by tab lever 62 to cause lateral bills 8, 10 (lateral bill 8 not shown in FIG. 4) to be maximally separated.

It is to be understood that another important feature of vaginal speculum 2 is the angular disposition of handle 26 relative to lower bill 20 such that handle 26 is disposed at an obtuse angle of approximately 130 degrees from the axis of lower bill 20, thereby reducing the incidence of handle 26 touching the body of the patient when upper bill 12 and lower bill 20 are inserted in the patient's vaginal opening.

FIG. 5 discloses an enlarged view, partly cut away, of the handle 26 and lift assembly 45 of the invention. Each of levers 56 and 57 is retained within a side 86, 88 respectively of guide frame 58. Guide frame 58 is fixed at its base 108 to slider bar 46. Ratchet arm 76 extends rearwardly from slider bar 46 near its joinder with arms 48 and 50 of yoke 44.

Slider bar 46 is slidable within channel 102 of handle 26. Button 100 may be depressed to unlock slider bar 46 from handle 26 in order to move slider bar 46 to a selected position along handle 26.

FIG. 6 depicts guide frame 58 in an enlarged bottom plan view wherein it is seen that levers 56 and 57 are disposed at rest spaced apart from base 108 of guide frame 58. A spring element 130 resists movement of levers 56 and 57 toward base 108 of guide frame 58. Slots 82, 84 within sides 86, 88 of guide frame 58 define the range of movement of levers 56, 57.

Figure 7:
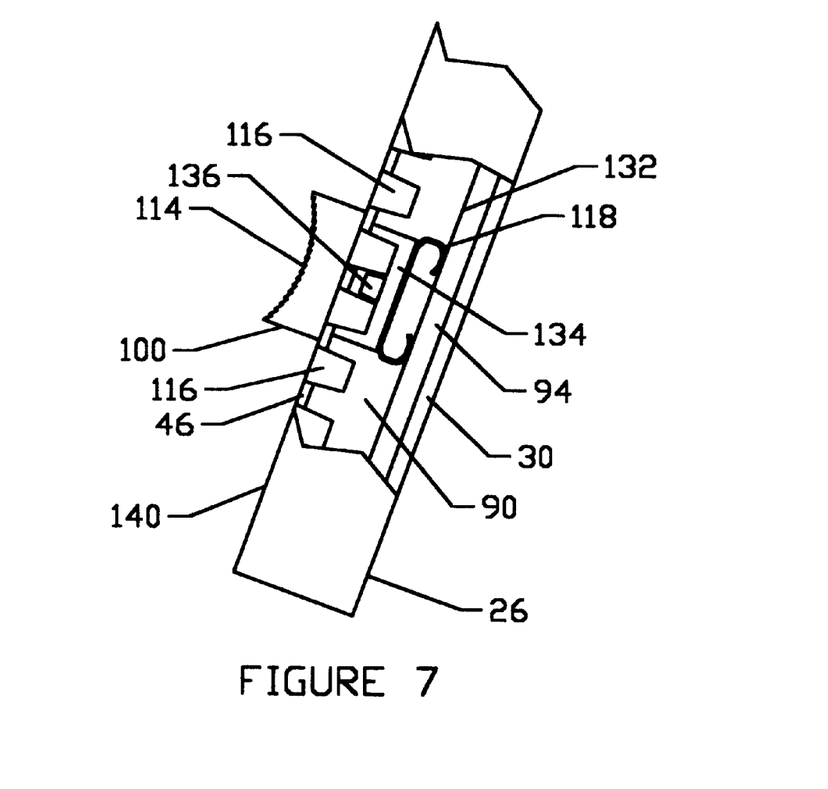
FIG. 7 is a partly cut away side plan of the handle of the preferred embodiment vaginal speculum.
Figure 8:
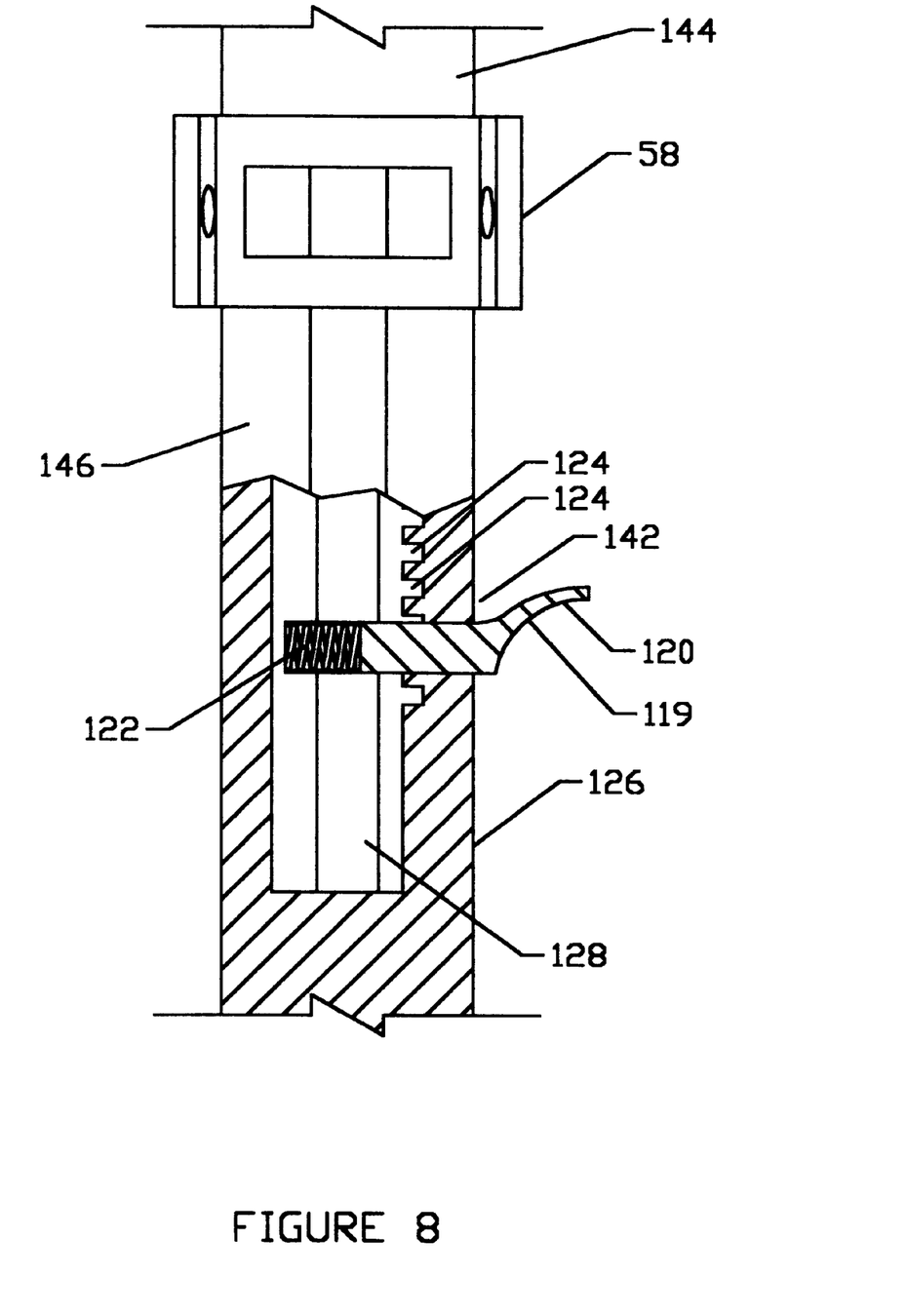
FIG. 8 is a partly cut away front view, partly in section of the handle of an alternate embodiment of the invention.

Referring now to FIGS. 7 and 8, the detail of the latch mechanism of the lift assembly 45 is disclosed. Handle 26 is generally hollow in its interior 90 and fiber optic cable 30 and duct 94 pass therethrough. An interior longitudinal wall 132 separates duct 94 and fiber optic cable 30 from interior 90 and provides a surface on which spring 118 of button 100 may bear. Button 100 is mounted to slider bar 46 of yoke 44. Button 100 is provided with laterally ridged upper surface 114 which is concave, thereby providing slip resistance for a user's thumb. Button 100 is slidable transversely within slider bar 46 such that a user may move slider bar 46 along channel 102 of handle 26 to a desired position and latched by operation of button 100. Button 100 is depressible into the interior 90 of handle 26 against the resistance of spring element 118. Button is provided at its lateral sides with a nub 136 which extends from the lateral sides 134 of button. Nub 136 provides a mechanical interference with pegs 116 which extend into interior 90 and depend from proximal outer wall 140 of handle 26. When button 100 is depressed, nub 136 is displaced from interference with pegs 116 and slider bar 46 may be moved longitudinally along channel 120 of handle 26. When the desired separation of upper bill member 4 and lower bill member 6 is achieved, button 100 may be released and spring 118 urges nub 136 into a space between an adjacent pair of pegs 116. Then upper bill 12 may be rotated about pivot pin 52 to retract upper tissues of the vaginal opening and lateral blades 8, 10 may be spread to retract side tissues of the vaginal opening.

An alternate embodiment lock mechanism 142 is disclosed in FIG. 8 wherein slider 146 of yoke 144 is provided with thumb lever 119 mounted thereto. Thumb lever 119 is transversely moveable when force is applied upon curved surface 120 by the user's thumb thereby displacing thumb lever 119 toward the left against the bias of compression spring 122. A tooth (not shown) mounted to thumb lever 119 is received between pairs of lateral projecting stubs 124 which are formed in handle 126 adjacent channel 128 when compression spring 122 is allowed to relax thereby fixing slider 146 longitudinally along handle 126.

Having described the invention, I claim:

1. A vaginal speculum comprising
    a first dilator blade having an integral handle member angularly extending therefrom,
    a second dilator blade having a yoke pivotably mounted thereto,
    the second dilator blade rotatable about said yoke,
    said second dilator blade rotatable relative to said first dilator blade,
    said yoke slidably mounted to said handle member for longitudinal movement therealong,
    a pair of retractor paddles retained to said yoke,
    the pair of retractor paddles selectively separable orthogonally to said rotation of said second dilator blade.

2. The vaginal speculum of claim 1 wherein
    said pair of retractor paddles resides between said first dilator blade and said second blade when said vaginal speculum is in a closed position with said second dilator blade touching said first dilator blade.

3. The vaginal speculum of claim 2 wherein
    said yoke comprises a U-shaped upper segment and a lower leg,
    the U-shaped upper segment having opposing arms,
    each of said retractor paddles is supported on a rotatable shaft,
    each of said shafts is retained to one of said opposing arms and is axially rotatable thereon,
    each of said shafts is substantially non-linear to the axis of said retractor paddle supported by said shaft.

4. The vaginal speculum of claim 2 wherein
    said yoke comprises a U-shaped upper segment and a lower leg,
    the U-shaped upper segment having opposing arms,
    said lower leg is received in a slot along said handle.

5. The vaginal speculum of claim 4 wherein
    ratchet and pawl means is provided on said handle and said leg respectively to selectively fix said leg along said handle at selected locations.

6. The vaginal speculum of claim 1 wherein
    said handle is provided with finger grooves therealong.

7. The vaginal speculum of claim 1 wherein
said handle is disposed at an obtuse angle to said first dilator blade.
8. The vaginal speculum of claim 7 wherein
said handle is disposed at an angle of approximately 130 degrees from the axis of said first dilator blade.
9. The vaginal speculum of claim 1 wherein
said first dilator blade having a reservoir therein adjacent said handle,
a conduit disposed through said handle, said conduit communicative with said basin to allow passage of fluids from said reservoir.
10. The vaginal speculum of claim 1 wherein
said first dilator blade having an inner concave surface,
a fiber optic cable mounted within said handle,
said fiber optic cable having a first end disposed upon said inner concave surface,
said fiber optic cable having a second end extending from said handle for coupling to a light source.
11. A vaginal speculum comprising
a first dilator blade having an integral handle member angularly extending therefrom,
a second dilator blade having a yoke pivotably mounted thereto,
said yoke slidably mounted to said handle member for longitudinal movement therealong,
said first dilator blade having an enlarged segment adjacent said handle,
said enlarged segment having an open topped basin therein,
a conduit disposed longitudinally through said handle, said conduit communicative with said basin to convey fluids from said basin to the exterior of said handle.
12. The vaginal speculum of claim 11 wherein
said first dilator blade has an inner concave surface,
a flexible fiber optic cable mounted within said handle,
said fiber optic cable having a first end disposed upon said inner concave surface,
said fiber optic cable having a second end extending from said handle for coupling to a light source.
13. The vaginal speculum of claim 11 wherein
said handle disposed at an obtuse angle to said first dilator blade,
said handle having molded depressions thereon for receiving the fingers of a user.
14. The vaginal speculum of claim 11 wherein
said second dilator blade rotatable about said yoke,
said second dilator blade rotatable relative to said first dilator blade,
a pair of retractor paddles retained to said yoke,
the pair of retractor paddles selectively separable orthogonally to said rotation of said second dilator blade,
said pair of retractor paddles resides between said first dilator blade and said second blade when said vaginal speculum is in a closed position with said second dilator blade touching said first dilator blade,
said yoke comprises a U-shaped upper segment having opposing arms and a lower leg,
said leg is received in a slot along said handle
each of said retractor paddles is supported on a rotatable shaft,
each of said shafts is retained to one of said opposing arms and is axially rotatable thereon,
each of said shafts is substantially perpendicular to the axis of said retractor paddle supported by said shaft.
15. A vaginal speculum comprising
a first dilator blade having an integral handle member angularly extending therefrom,
a second dilator blade having a yoke pivotably mounted thereto,
said yoke slidably mounted to said handle member for longitudinal movement therealong,
said first dilator blade having an inner concave surface,
a flexible fiber optic cable mounted within said handle,
said fiber optic cable having a first end disposed upon said inner concave surface,
said fiber optic cable having a second end extending from said handle for coupling to a light source.
16. The vaginal speculum of claim 15 wherein
said second dilator blade rotatable about said yoke,
said second dilator blade rotatable relative to said first dilator blade,
a pair of retractor paddles retained to said yoke,
the pair of retractor paddles selectively separable orthogonally to said rotation of said second dilator blade,
said pair of retractor paddles resides between said first dilator blade and said second blade when said vaginal speculum is in a closed position with said second dilator blade touching said first dilator blade.
17. The vaginal speculum of claim 16 wherein
said yoke comprises a U-shaped upper segment and a lower leg,
said U-shaped upper segment having opposing arms,
each of said retractor paddles is supported on a rotatable shaft,
each of said shafts is retained to one of said opposing arms and is axially rotatable thereon,
each of said shafts is substantially perpendicular to the axis of said retractor paddle supported by said shaft.
18. A vaginal speculum comprising
a first dilator blade having an integral handle member angularly extending therefrom,
a second dilator blade having a yoke pivotably mounted thereto,
said yoke slidably mounted to said handle member for longitudinal movement therealong,
said handle disposed at an obtuse angle to said first dilator blade,
said handle having molded depressions thereon for receiving the fingers of a user.
19. The vaginal speculum of claim 18 wherein
said handle disposed at an angle of approximately 130 degrees to said first dilator blade.
20. The vaginal speculum of claim 19 wherein
a pair of retractor paddles is retained to said yoke,
the pair of retractor paddles selectively separable orthogonally to said rotation of said second dilator blade,
said second dilator blade rotatable about said yoke relative to said first dilator blade,
said pair of retractor paddles resides between said first dilator blade and said second blade when said vaginal speculum is in a closed position with said second dilator blade touching said first dilator blade,
said yoke comprises a U-shaped upper segment and a lower leg, said leg is received in a slot along said handle, said U-shaped upper segment having opposing arms, each of said retractor paddles is supported on a rotatable shaft, each of said shafts is retained to one of said opposing arms and is axially rotatable thereon, each of said shafts is substantially non-linear to the axis of said retractor paddle supported by said shaft, said first dilator blade having an open topped reservoir therein adjacent said handle, a conduit disposed through said handle, said conduit communicative with said basin to allow passage of fluids from said reservoir, said first dilator blade having an inner concave surface, a fiber optic cable mounted within said handle, said fiber optic cable having a first end disposed upon said inner concave surface, said fiber optic cable having a second end extending from said handle for coupling to a light source.

21. The vaginal speculum of claim 18 wherein said handle having a planar rear side disposed rearwardly of said first dilator blade, said molded depressions surrounding said handle except said rear side.

22. A vaginal speculum comprising a first dilator blade having an integral handle member angularly extending therefrom, a second dilator blade having a support member mounted thereto, said support member slidably mounted to said handle member for longitudinal movement therealong, said second dilator blade rotatable relative to said first dilator blade, a pair of retractor paddles retained to said support member, the pair of retractor paddles selectively separable orthogonally to said longitudinal movement of said support mpember.

23. The vaginal speculum of claim 22 wherein said pair of retractor paddles resides between said first dilator blade and said second blade when said vaginal speculum is in a closed position with said second dilator blade touching said first dilator blade.

* * * * *